United States Patent
Murata et al.

(10) Patent No.: US 11,802,825 B2
(45) Date of Patent: Oct. 31, 2023

(54) PLATELET AGGREGATION ANALYSIS METHOD, PLATELET AGGREGATION ANALYSIS DEVICE, PROGRAM FOR ANALYZING PLATELET AGGREGATION, AND PLATELET AGGREGATION ANALYSIS SYSTEM

(71) Applicant: Sony Corporation, Tokyo (JP)

(72) Inventors: Aya Murata, Kanagawa (JP); Yoshihito Hayashi, Chiba (JP); Kenzo Machida, Kanagawa (JP); Seungmin Lee, Kanagawa (JP)

(73) Assignee: Sony Corporation, Tokyo (JP)

( * ) Notice: Subject to any disclaimer, the term of this patent is extended or adjusted under 35 U.S.C. 154(b) by 1157 days.

(21) Appl. No.: 16/337,598

(22) PCT Filed: Jul. 21, 2017

(86) PCT No.: PCT/JP2017/026398
§ 371 (c)(1),
(2) Date: Mar. 28, 2019

(87) PCT Pub. No.: WO2018/066207
PCT Pub. Date: Apr. 12, 2018

(65) Prior Publication Data
US 2019/0346352 A1    Nov. 14, 2019

(30) Foreign Application Priority Data
Oct. 5, 2016    (JP) .................................. 2016-197156

(51) Int. Cl.
*G01N 11/00* (2006.01)
*G01N 19/00* (2006.01)
(Continued)

(52) U.S. Cl.
CPC .............. *G01N 11/00* (2013.01); *G01N 19/00* (2013.01); *G01N 27/22* (2013.01); *G01N 33/49* (2013.01);
(Continued)

(58) Field of Classification Search
CPC .. G01N 33/86; G01N 33/4905; G01N 27/221; G01N 11/00; G01N 2021/056;
(Continued)

(56) References Cited

U.S. PATENT DOCUMENTS 4,788,139 A  *  11/1988  Ryan ...................... G01N 33/86
                                                            435/13
6,534,277 B1 *   3/2003  Hancock .......... A61K 39/39541
                                                             435/7.1
(Continued)

FOREIGN PATENT DOCUMENTS

CN    2250523 Y       3/1997
CN    2250523 Y  *    3/1997
(Continued)

OTHER PUBLICATIONS

International Search Report and Written Opinion and English translations thereof dated Oct. 24, 2017 in connection with International Application No. PCT/JP2017/026398.
(Continued)

*Primary Examiner* — Harshad R Patel
*Assistant Examiner* — Gedeon M Kidanu
(74) *Attorney, Agent, or Firm* — Wolf, Greenfield & Sacks, P.C.

(57) ABSTRACT

A measurement method of simply and quickly measuring platelet aggregation, is provided.
The measurement method is a platelet aggregation analysis method, including:
a step of adding a platelet-inducing substance and a calcium salt to a platelet-containing specimen;
(Continued)

a step of stirring the platelet-containing specimen; and a step of acquiring measurement data of an electrical characteristic and/or viscoelasticity of the platelet-containing specimen.

11 Claims, 7 Drawing Sheets

(51) Int. Cl.
   *G01N 27/22*  (2006.01)
   *G01N 33/49*  (2006.01)
   *G01N 33/86*  (2006.01)
(52) U.S. Cl.
   CPC ..... *G01N 33/86* (2013.01); *G01N 2011/0066* (2013.01)
(58) Field of Classification Search
   CPC ... G01N 2021/6441; G01N 2021/7763; G01N 2021/7786; G01N 2021/7793; G01N 2035/00891; G01N 21/05; G01N 21/5907; G01N 21/6428; G01N 21/82; G01N 27/02; G01N 27/021; G01N 27/026; G01N 33/49; G01N 33/5088; G01N 35/00722; A61K 2039/505; A61K 2300/00; A61K 39/39541; C07K 16/2875; C12Q 1/6883; C12Q 2600/158
   See application file for complete search history.

(56) References Cited

U.S. PATENT DOCUMENTS

| | | | |
|---|---|---|---|
| 2005/0015001 A1 | 1/2005 | Lee et al. | |
| 2009/0004681 A1 | 1/2009 | Hoshiko et al. | |
| 2012/0238026 A1* | 9/2012 | Hayashi | G01N 33/86 436/69 |
| 2014/0065715 A1* | 3/2014 | Shin | G01N 33/86 436/69 |
| 2014/0186217 A1 | 7/2014 | Hayashi et al. | |
| 2015/0323480 A1* | 11/2015 | Brun | G01N 33/4905 422/82.01 |
| 2015/0338330 A1 | 11/2015 | Hosokawa et al. | |
| 2017/0023596 A1 | 1/2017 | Hosokawa et al. | |

FOREIGN PATENT DOCUMENTS

| | | | | | |
|---|---|---|---|---|---|
| CN | 101881737 | A | | 11/2010 | |
| CN | 101881737 | B | * | 8/2011 | |
| CN | 202372514 | U | | 8/2012 | |
| CN | 202372514 | U | * | 8/2012 | |
| EP | 2009446 | A1 | | 12/2008 | |
| EP | 2500726 | A1 | | 9/2012 | |
| EP | 2937699 | A1 | | 10/2015 | |
| EP | 2950087 | A1 | | 12/2015 | |
| EP | 3130920 | A1 | | 2/2017 | |
| JP | 2009-008503 | A | | 1/2009 | |
| JP | 2010-181400 | A | | 8/2010 | |
| JP | 2012-194087 | A | | 10/2012 | |
| JP | 2012194087 | A | * | 10/2012 | ......... G01N 33/4905 |
| JP | 5691168 | B2 | * | 4/2015 | .......... G01N 27/026 |
| JP | 2015-190804 | A | | 11/2015 | |
| WO | WO 2004/093641 | A2 | | 11/2004 | |
| WO | WO 2014/098242 | A1 | | 6/2014 | |
| WO | WO 2014/115478 | A1 | | 7/2014 | |
| WO | WO 2015/156322 | A1 | | 10/2015 | |
| WO | WO-2017093266 | A2 | * | 6/2017 | ............. G01N 21/05 |
| WO | WO-2017141508 | A | | 8/2017 | |
| WO | WO-2017141508 | A1 | * | 8/2017 | ............. G01N 11/00 |

OTHER PUBLICATIONS

International Preliminary Report on Patentability and English translation thereof dated Apr. 18, 2019 in connection with International Application No. PCT/JP2017/026398.

* cited by examiner

40 PLATELET AGGREGATION ANALYSIS SYSTEM

PLATELET AGGREGATION ANALYSIS METHOD, PLATELET AGGREGATION ANALYSIS DEVICE, PROGRAM FOR ANALYZING PLATELET AGGREGATION, AND PLATELET AGGREGATION ANALYSIS SYSTEM

CROSS-REFERENCE TO RELATED APPLICATIONS

This application claims the benefit under 35 U.S.C. § 371 as a U.S. National Stage Entry of International Application No. PCT/JP2017/026398, filed in the Japanese Patent Office as a Receiving Office on Jul. 21, 2017, which claims priority to Japanese Patent Application Number JP2016-197156, filed in the Japanese Patent Office on Oct. 5, 2016, each of which is hereby incorporated by reference in its entirety.

TECHNICAL FIELD

The present invention relates to a platelet aggregation analysis method, a platelet aggregation analysis device, a program for analyzing platelet aggregation, and a platelet aggregation analysis system.

BACKGROUND ART

An anticoagulation therapy or an antiplatelet therapy is an indispensable treatment method for thrombosis prevention, and the usefulness thereof has been demonstrated by an extensive clinical test.

However, there is a case where the antiplatelet therapy has a low effect of reducing artery thrombosis, compared to a brain infarction reduction effect of the anticoagulation therapy.

It is considered that one of the reasons is that in the anticoagulation therapy, a medicinal effect is suitably monitored for each patient, according to an international normalized ratio of prothrombin time (PT-INR) or a thrombo test, but in the antiplatelet therapy, a monitoring method has not yet established even though it has been reported that there is a considerable individual difference in the sustainment of the receptivity or the effect of an antiplatelet agent.

Accordingly, in a case where the medicinal effect can be suitably monitored by an easily comprehensible method even in the antiplatelet therapy, the antiplatelet therapy will be a means for searching a proper using method of drugs in each case, and improvement in a treatment effect can be expected.

Here, the most basic function of platelets is pressure-sensitive adhesion and aggregation. A platelet aggregation examination method of determining an attachment state between the platelets, is most popular as a method of quantitatively measuring the basic function. Specifically, there are 1) a permeation rate method, 2) an impedance method, 3) a particle calculation method, and the like. In such an examination method, it is possible to know the details of a decrease and an increase in a blood examination function, according to the type or the concentration of an aggregation-inducing substance to be used. In particular, the permeation rate method is general as a daily examination.

1) The permeation rate method is a method of temporally quantifying platelet aggregation by adding a platelet stimulating substance, and by using a fact that the transparency of platelet-rich blood plasma (PRP) increases according to the platelet aggregation in the PRP.

The permeation rate method includes problems such as:
(i) a problem that the separation of the blood plasma is essential, and thus, a test body treatment until the measurement, is complicated, the amount of PRP obtained by a centrifugal condition is changed, a collection rate of the platelet is not constant, and when a PRP separation operation is performed, platelets having a high density are precipitated along with red blood cells, and such an aggregation manner is not capable of being observed;
(ii) a problem that the strength (an aggregation rate) of the platelet depends on the number of platelets in the aggregation PRP to an extent, and thus, in a case where the number of platelets is less than or equal to $100000/\mu l$, a difference between light absorbances before and after the aggregation is small, and a slight change is not capable of being detected;
(iii) a problem that an examination using opacified blood plasma such as whole blood and chyle blood plasma, is not capable of being performed; and
(iv) a problem that a correlation between the formation of a platelet aggregate and light permeability is bad.

2) The impedance method is a method of detecting platelet aggregation as a change in electrical resistance between electrodes, and is a method in which the platelet aggregation in the whole blood can be observed, and the entire aggregation manner of the platelet can be observed since there is no centrifugal operation.

The impedance method includes problems such as:
(v) a problem that an initial decrease in the electrical resistance is due to the presence of red blood cells between the electrodes, and it is difficult to determine an initial state of the platelet aggregation; and
(vi) a problem that an aggregation pattern is not stable, compared to the permeation rate method.

3) The particle calculation method is a method of knowing an aggregation manner by calculating the number of single platelets not involved in the formation of a platelet aggregate or an aggregate, with a Coulter counter.

The particle calculation method includes problems such as:
(vii) a problem that the manipulation is complicated;
(viii) a problem that a sequential change is not capable of being recorded; and
(ix) a problem that platelet dissolution according to an aggregation-inducing substance is erroneously calculated as a decrease in the single platelet.

On the other hand, recently, a method of performing dielectric measurement of a blood coagulation process, has been devised as a method in which blood coagulability measurement can be simply and accurately evaluated (Patent Document 1).

Such a method is a method in which a condenser-like specimen portion including a pair of electrodes and the like, is filled with blood, an alternating electric field is applied to the specimen portion, and thus, a change in a dielectric constant according to the blood coagulation process is measured.

Here, blood is collected from the vein of a blood test body, by using a citric acid as an anticoagulation agent, an aqueous solution of calcium chloride is added to the blood test body immediately before the measurement is started, and thus, a blood coagulation reaction progresses by cancelling an anticoagulation action of the citric acid. Data obtained as described above is analyzed according to a predetermined algorithm, and thus, it is possible to obtain a parameter relevant to blood coagulation, such as a blood coagulation time.

Then, a blood coagulation system analysis method of acquiring information associated with the coagulability of the blood has developed on the basis of a change occurring in a complex dielectric constant spectrum, measured in the blood coagulation process by further studying the dielectric measurement of the blood coagulation process, and by adding a substance of activating or inactivating the platelet to the blood (Patent Document 2).

In the blood coagulation system analysis method, in a case of using a platelet activating substance, it is possible to acquire information associated with the coagulability of the platelet included in the blood in an inactive state, on the basis of a change occurring in the complex dielectric constant spectrum due to platelet activation. In addition, in a case of using a platelet inactivating substance, it is possible to acquire information associated with the coagulability of the platelet included in the blood in an active state, on the basis of a change occurring in the complex dielectric constant spectrum due to platelet inactivation.

CITATION LIST

Patent Document

Patent Document 1: Japanese Patent Application Laid-Open No. 2010-181400
Patent Document 2: Japanese Patent Application Laid-Open No. 2012-194087

SUMMARY OF THE INVENTION

Problems to be Solved by the Invention

However, in the method of performing the dielectric measurement of the blood coagulation process and the blood coagulation system analysis method, it is necessary to set in advance a shortening width Ats (a reference value) of the blood coagulation time, which becomes a reference, by using a sample having normal coagulability (the whole blood).

In addition, when the coagulation reaction progresses, an accelerating reagent is not added, and thus, a measurement time is long. In a case where the accelerating reagent is added, a difference according to a platelet function disappears.

Solutions to Problems

Therefore, the present inventors have conducted intensive studies in order to provide a simple and quick measurement method of platelet aggregation.

Then, the present inventors have found that a small amount of aqueous solution of calcium chloride and a platelet-inducing substance are added to the whole blood, and are stirred for constant time, and then, a difference occurs between a change in a dielectric constant to be measured in a non-disturbance coagulation (a natural blood coagulation) process of the blood, and a change in a dielectric constant in a case where a non-platelet-inducing substance is added, and thus, have completed the present technology.

That is, the present technology provides a platelet aggregation analysis method, including:
a step of adding a platelet-inducing substance and a calcium salt to a platelet-containing specimen;
a step of stirring the platelet-containing specimen; and
a step of acquiring measurement data of an electrical characteristic and/or viscoelasticity of the platelet-containing specimen.

It is preferable that the measurement data of the electrical characteristic is a dielectric constant of the platelet-containing specimen.

In addition, the measurement data of the viscoelasticity may be measurement data of the platelet-containing specimen according to a rheometer.

In the platelet aggregation analysis method of the present technology, a step of analyzing platelet aggregation, on the basis of the measurement data of the electrical characteristic and/or the viscoelasticity of the platelet-containing specimen, and measurement data of an electrical characteristic and/or viscoelasticity, acquired from a platelet-containing specimen to which the platelet-inducing substance is not added, can be further included.

The platelet-containing specimen may be blood or blood plasma.

In addition, the blood or the blood plasma can be used by being collected from a test subject dosed with an antiplatelet aggregation agent and/or an anticoagulation agent.

The present technology also provides a platelet aggregation analysis device, including:
a biological sample retention unit configured to retain a platelet-containing specimen;
a medical agent supply unit configured to supply a platelet-inducing substance and/or a calcium salt to the platelet-containing specimen;
a stirring mechanism configured to stir the platelet-containing specimen; and
a measurement unit configured to measure an electrical characteristic of the platelet-containing specimen.

In addition, the present technology further provides
a program for analyzing platelet aggregation, allowing a computer to execute: analyzing platelet aggregation, on the basis of measurement data of an electrical characteristic and/or viscoelasticity, acquired from a platelet-containing specimen to which a platelet-inducing substance and a calcium salt are added, and measurement data of an electrical characteristic and/or viscoelasticity, acquired from a platelet-containing specimen to which the platelet-inducing substance is not added.

In the analyzing, the measurement data of the electrical characteristic and/or the viscoelasticity, acquired from the platelet-containing specimen to which the platelet-inducing substance and the calcium salt are added, may be compared with the measurement data of the electrical characteristic and/or the viscoelasticity, acquired from the platelet-containing specimen to which the platelet-inducing substance is not added.

Further, the present technology is capable of providing a platelet aggregation analysis system, including:
a platelet aggregation analysis device including:
a biological sample retention unit configured to retain a platelet-containing specimen;
a medical agent supply unit configured to supply a platelet-inducing substance and/or a calcium salt to the platelet-containing specimen; a stirring mechanism configured to stir the platelet-containing specimen; and
a measurement unit configured to measure an electrical characteristic of the platelet-containing specimen,
a computer with a program for analyzing platelet aggregation being built in the platelet aggregation analysis device, the program allowing the computer to execute analyzing platelet aggregation, on the basis of measurement data of the electrical characteristic and/or viscoelasticity, acquired from the platelet-containing specimen to which the platelet-inducing substance and the calcium salt are added, and measurement data of an electrical characteristic and/or viscoelasticity, acquired from a platelet-containing specimen to which the platelet-inducing substance is not added; and a display device configured to display an analysis result.

BRIEF DESCRIPTION OF DRAWINGS

FIG. 5-1 is a graph showing a measurement result of a test body according to impedance aggregation measurement.

FIG. 5-2 is a graph showing a measurement result of the test body according to a dielectric constant.

FIG. 6-1 is a graph showing an example of an analysis result based on the measurement result according to the dielectric constant.

FIG. 6-2 is a graph showing an example of the analysis result based on the measurement result according to the dielectric constant.

FIG. 7-1 is a graph showing a correlative relationship between measurement data according to the dielectric constant and a measurement data parameter (AUC(U)) according to the impedance aggregation measurement.

FIG. 7-2 is a graph showing a correlative relationship between the measurement data according to the dielectric constant and a measurement data parameter (Aggregation (AU)) according to the impedance aggregation measurement.

FIG. 9-1 is a graph showing a correlative relationship between data of the dielectric clot strength based on the dielectric constant and the measurement data parameter (AUC(U)) according to the impedance aggregation measurement.

FIG. 9-2 is a graph showing a correlative relationship between the data of the dielectric clot strength based on the dielectric constant and the measurement data parameter (Aggregation (AU))) according to the impedance aggregation measurement.

MODE FOR CARRYING OUT THE INVENTION

Figure 1:
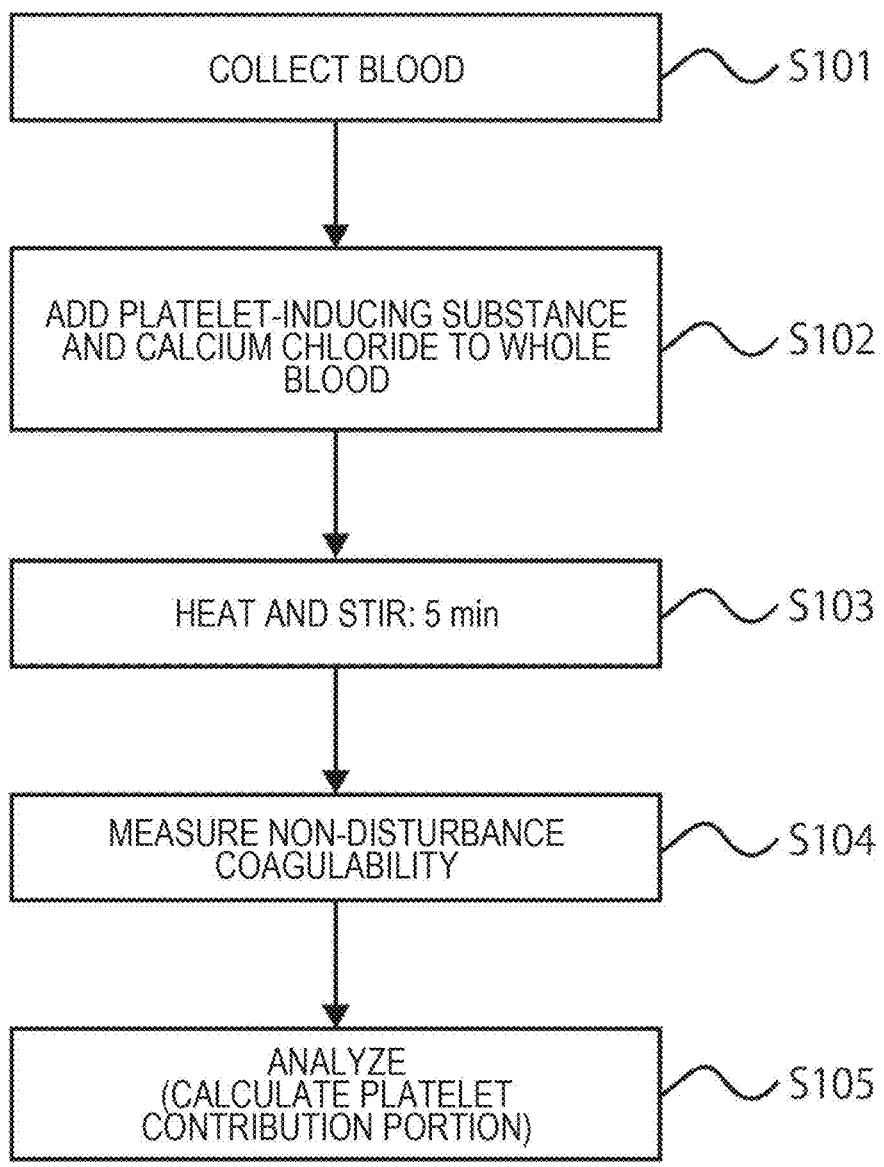
FIG. 1 is a diagram illustrating a measurement flow in a platelet aggregation analysis method.

Hereinafter, a preferred mode for carrying out the present technology, will be described. Furthermore, the following embodiment indicates a representative embodiment of the present technology, and with this arrangement, the scope of the present technology is not narrowly interpreted. Furthermore, the description will be given in the following order.
1. Platelet Aggregation Analysis Method
2. Platelet Aggregation Analysis Device
3. Program for Analyzing Platelet Aggregation
4. Platelet Aggregation Analysis System
5. Example
(1) Method
(2) Result
(3) Analysis Example 1
(4) Analysis Example 2
6. Conclusion 1. Platelet Aggregation Analysis Method A platelet aggregation analysis method of the present technology, includes:

Step A: a step of adding a platelet-inducing substance and a calcium salt to a platelet-containing specimen;

Step B: a step of stirring the platelet-containing specimen; and

Step C: a step of acquiring measurement data of an electrical characteristic and/or viscoelasticity of the platelet-containing specimen.

In Step A, the platelet-containing specimen to which the platelet-inducing substance and the calcium salt are added, is stirred in Step B, and thus, the platelets activated by the platelet-inducing substance, are aggregated. In Step C, the platelet that reacted in Step B, does not contribute to a response, but the platelet that did not react, responds in a process of a blood coagulation reaction.

The platelet-containing specimen that is an analysis target of the present technology, is not particularly limited, but examples of the platelet-containing specimen include the blood (the whole blood) from humans or mammals, blood plasma, artificial blood, and the like. In addition, the platelet-containing specimen may be a specimen collected from a test subject dosed with an antiplatelet aggregation agent, an anticoagulation agent, or both of the antiplatelet aggregation agent and the anticoagulation agent.

The platelet-inducing substance used in Step A, is a substance of causing or suppressing the aggregation of the platelet. The platelet-inducing substance, for example, is collagen (COL), epinephrine, ristocetin, thrombin, thromboxane A2 (TAX2), thrombin receptor activating protein (TRAP), adenosine diphosphate (ADP), arachidonic acid (AA), serotonin, adrenaline, and noradrenaline.

For example, in a case of the thrombin receptor activating protein (TRAP), an added concentration of the platelet-inducing substance (the final concentration at the time of being added to the specimen), is preferably greater than or equal to 1 µM and less than or equal to 100 µM, is more preferably greater than or equal to 3 µM and less than or equal to 80 µM, and is even more preferably greater than or equal to 5.4 µM and less than or equal to 62 µM.

In a case of the adenosine diphosphate (ADP), the added concentration of the platelet-inducing substance is preferably greater than or equal to 0.1 µM and less than or equal to 100 µM, is more preferably greater than or equal to 0.5 µM and less than or equal to 30 µM, and is even more preferably greater than or equal to 1.0 µM and less than or equal to 12.5 µM.

In a case of the arachidonic acid (AA), the added concentration of the platelet-inducing substance is preferably greater than or equal to 0.01 mM and less than or equal to 10 mM, is more preferably greater than or equal to 0.05 mM and less than or equal to 5.0 mM, and is even more preferably greater than or equal to 0.08 mM and less than or equal to 1.0 mM.

The calcium salt (calcium chloride or the like) used in Step A, is a substance for solving an anticoagulation action due to the citric acid added to the test body at the time of collecting the blood, according to a calcium ion to be contained.

An added concentration of the calcium chloride (a reagent concentration of the calcium chloride) is not particularly limited insofar as being a concentration having a platelet coagulation accelerating effect, and is preferably greater than or equal to 150 mM and less than or equal to 250 mM, is more preferably greater than or equal to 170 mM and less than or equal to 230 mM, and is even more preferably greater than or equal to 185 mM and less than or equal to 215 mM.

In Step A, a timing when the platelet-inducing substance and the calcium salt are added to the platelet-containing specimen, is not particularly limited, and in the present technology, the platelet-inducing substance and the calcium salt can be simultaneously added. Then, in Step B described above, the platelet-containing specimen, the platelet-inducing substance, and the calcium salt are stirred, and then, in Step C, data of platelet coagulability is acquired.

A stirring condition in Step B described above, is not particularly limited insofar as being a condition in which a platelet coagulation reaction of the platelet-containing specimen is not hindered, and for example, the stirring is performed at 37° C. A stirring rate and a strength are also not particularly limited, but it is preferable that the stirring rate and the strength are considered in advance according to a stirring method or the type of inducing substance. The stirring method is also not particularly limited, and examples of the stirring method include suction and discharge with a pipette, the use of a stirrer, and the like. It is known that 5 minutes is a rough standard as a time for the platelet to react with the platelet-inducing substance, and to be aggregated, according to the consideration of the present technology, but a stirring time is not particularly limited thereto, and is preferably 3 minutes to 6minutes. The stirring time is shortened or prolonged, according to the stirring method or the type of inducing substance .

In Step C described above, the electrical characteristic and/or the viscoelasticity of the platelet-containing specimen, are measured.

Here, examples of the electrical characteristic are capable of including a dielectric constant, impedance, admittance, capacitance, conductance, an electrical conductivity, a phase angle, and the like. In a case of the dielectric constant, the dielectric constant may be measured according to a measurement method of a coagulation process described in the specification of Japanese Patent No. 5691168 and the specification of Japanese Patent No. 5768422.

In addition, the viscoelasticity can be measured by a rheometer. Examples of the rheometer include a rotation thrombo elastometry, a thrombo elastography, and ReoRox (Trademark). Examples of a commercially available device include a thrombo elastography (TEG (Registered Trademark)) blood coagulation analysis device (manufactured by Haemonetics Corporation), a rotation thrombo elastometry (ROTEM (Registered Trademark)) blood coagulation analysis device (TEM group, Basel, Switzerland), and the like.

For example, a platelet-containing specimen to which the calcium salt is added but the platelet-inducing substance is not added, maybe used as a control sample at the time of measuring the platelet aggregation.

The measurement data of the platelet-containing specimen is compared with measurement data acquired from the platelet-containing specimen that is the control sample described above, to which the platelet-inducing substance is not added, and thus, it is possible to analyze the platelet aggregation. The comparison, for example, can be performed by calculating a difference in the data, a ratio, and a difference in the area of a measurement waveform.

Furthermore, as described above, there are various platelet-inducing substances such as TRAP, ADP, and AA, and the functions of such platelet-inducing substances in a coagulation system are different from each other.

Therefore, in a case where a plurality of the same platelet-containing specimens is prepared, a plurality of platelet-inducing substances is selected, and different platelet-inducing substances and the calcium salt are respectively added to the platelet-containing specimens, and are stirred, and thus, the electrical characteristic and/or the viscoelasticity are measured, and data comparison is performed, it is possible to consider the platelet coagulability corresponding to the platelet-inducing substance. Further, the measurement result can be compared with a measurement result of the control sample in which a normal saline solution, a buffer solution, or the like, with less influence on the platelet, is used instead of the platelet-inducing substance.

The platelet aggregation analysis method of the present technology, for example, can be performed according to a measurement flowchart illustrated in FIG. 1.

First, the blood is collected from the test subject (S101). The platelet-inducing substance and the calcium salt are added to the whole blood (S102). Such an operation can be performed in one step. After the platelet-inducing substance and the calcium salt are added, the whole blood is stirred under a heating condition (S103). The stirring time, for example, is 5 minutes.

Next, the blood coagulability measurement is performed (S104). The measurement can be performed in a non-stirring state. Such a step is non-disturbance coagulability measurement in which a natural blood coagulation process is measured without further adding an accelerating reagent or the like. In addition, the blood coagulability measurement may be temporally performed, or a time from when the measurement is started, may be designated, and the coagulability at the time point may be measured.

Finally, the obtained measurement data is analyzed, and a platelet contribution portion in the blood coagulation is calculated (S105).

2. Platelet Aggregation Analysis Device

A platelet aggregation analysis device of the present technology includes: a biological sample retention unit configured to retain a platelet-containing specimen; a medical agent supply unit configured to supply a platelet-inducing substance and/or a calcium salt to the platelet-containing specimen; a stirring mechanism configured to stir the platelet-containing specimen; and a measurement unit configured to measure an electrical characteristic of the platelet-containing specimen.

Figure 2:
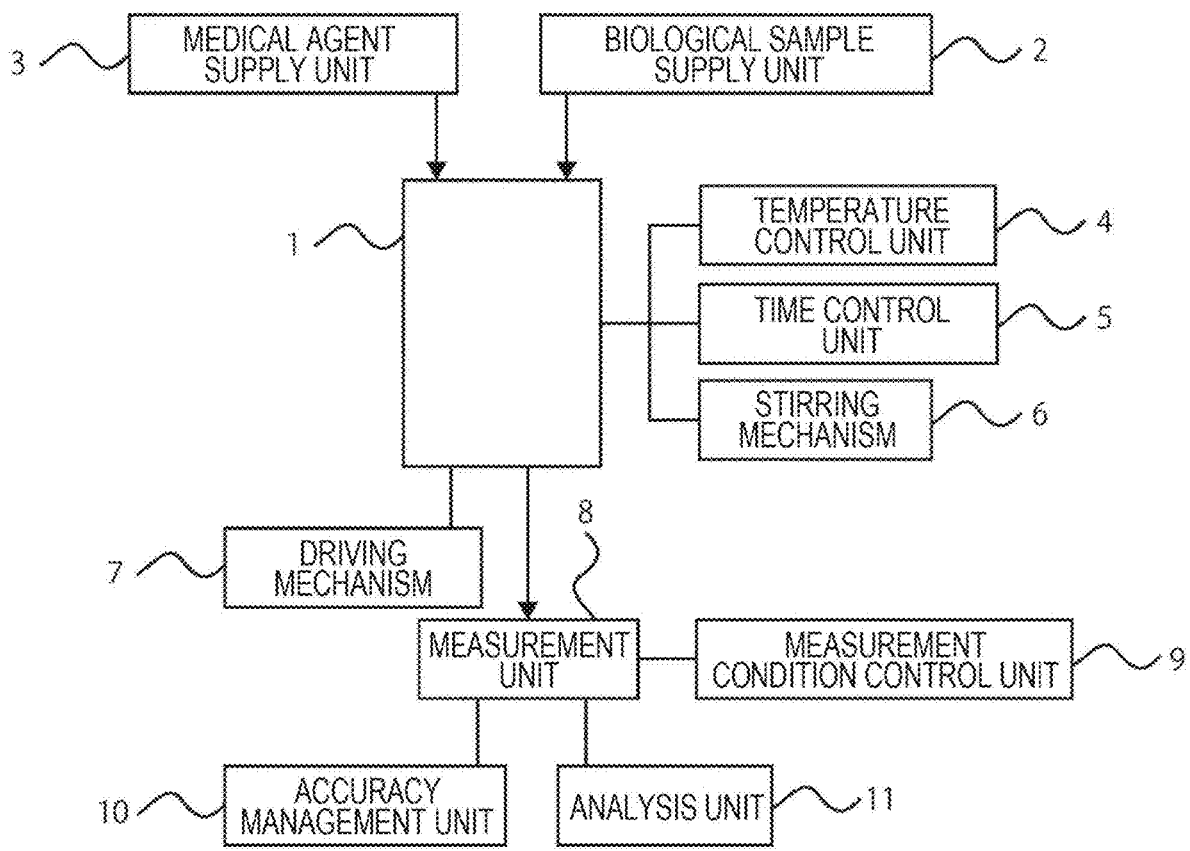
FIG. 2 is a diagram illustrating the outline of a configuration of a platelet aggregation analysis device.

The outline of the configuration of the platelet aggregation analysis device, is illustrated in FIG. 2.

A biological sample retention unit 1 retains the platelet-containing specimen supplied from a biological sample supply unit 2, and performs the stirring with respect to the platelet-containing specimen, and the platelet-inducing substance and the calcium salt, supplied from the medical agent supply unit 3.

A stirring mechanism 6 is operated to stir the platelet-containing specimen, the platelet-inducing substance, and the calcium salt, supplied to the biological sample retention unit 1. A stirring method is not particularly limited, and for example, the stirring can be performedby using an electric pipette, a stirrer, and a device with a stirring function.

The stirring is performed for a constant time in order for the reaction of the platelet.

A temperature control unit 4 and a time control unit 5 control the condition in the biological sample retention unit. For example, the temperature control unit 4 performs control such that the platelet-containing specimen is retained at a constant temperature. The time control unit 5 controls a time for which the platelet-containing specimen is retained in the biological sample retention unit 1, the stirring time, or the like.

A driving mechanism 7 performs a driving operation of the temperature control unit 4 or the stirring mechanism 6, an operation relevant to the biological sample retention unit 1, such as transferring the platelet-containing specimen.

A measurement unit 9 adds the platelet-inducing substance and/or the calcium salt to the platelet-containing specimen, and stirs them, and then, measures the dielectric constant. A rheometer may be used as the measurement unit 9.

A measurement condition control unit 9 sets and adjusts a temperature condition or a measurement time condition suitable for the measurement method. In addition, the measurement condition control unit 9 controls a frequency used for measurement, a measurement interval, or the like, at the time of performing dielectric constant measurement in the measurement unit 8.

An accuracy management unit 10 performs management of data such that a measurement difference, a background variation, or the like in the measurement unit 8 does not occur, monitoring of a state of each unit of the device, and the like.

An analysis unit 11 analyzes the platelet contribution portion in the blood coagulation, on the basis of the measurement data of the dielectric constant or the viscoelasticity. The analysis can be performedby using a program for analyzing platelet aggregation, as described later.

Furthermore, the analysis unit 11 may further include an output control unit configured to output an analysis result, a display device configured to display the analysis result, a storage unit configured to store the measurement data or the analysis result, and the like.

3. Program for Analyzing Platelet Aggregation

A program for analyzing platelet aggregation to be used in the present technology, allowing a computer to execute: analyzing platelet aggregation, on the basis of measurement data of an electrical characteristic and/or viscoelasticity, acquired from a platelet-containing specimen to which a platelet-inducing substance and a calcium salt are added, and measurement data of an electrical characteristic and/or viscoelasticity, acquired from a platelet-containing specimen to which the platelet-inducing substance is not added.

The program is provided in a storage medium.

The platelet-containing specimen to which the platelet-inducing substance is not added, can be used as the control sample. For example, a specimen to which the calcium salt is added, and a specimen to which a normal saline solution or a buffer solution is added, can be a control sample. By preparing the control sample, it is possible to calculate the platelet contribution portion by comparing and considering a difference in data, occurring due to the presence or absence of the addition of the platelet-inducing substance.

Figure 3:
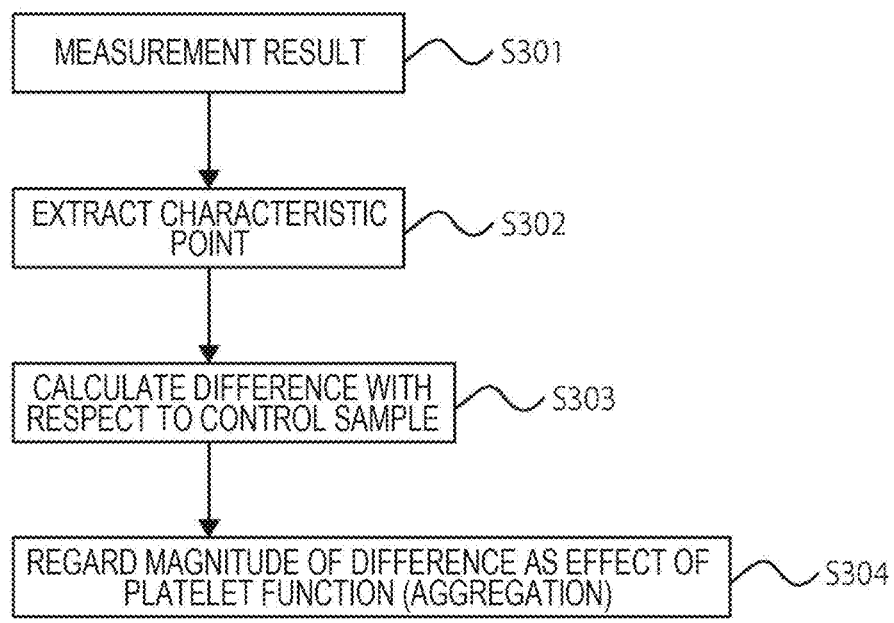
FIG. 3 is a diagram illustrating an analysis flow performed according to a program for analyzing platelet aggregation.

In FIG. 3, a flowchart of analysis performed by the program, is illustrated.

A characteristic point is extracted (S302), from the data of the measurement result obtained by the measurement unit 9 of the platelet aggregation analysis device (S301). The characteristic point, for example, is a point at which the measurement result of the control sample and the specimen starts to be stable, a point at which a coagulation time of the platelet is set, and the like. The characteristic point, for example, can be a specific time that has elapsed after the platelet-inducing substance and/or the calcium salt are added to the platelet-containing specimen, and are stirred.

A difference between measurement values of the platelet-containing specimen to which the platelet-inducing substance and the calcium salt are added, and the platelet-containing specimen to which the calcium salt is added, is calculated at the characteristic point (S303), and the result thereof is output.

The magnitude of the difference is set to the effect of a platelet function (S304). That is, it is determined that the platelet function (aggregation) is high in the platelet-containing specimen to which the platelet-inducing substance and the calcium salt are added, as the difference is large.

4. Platelet Aggregation Analysis System

Figure 4:
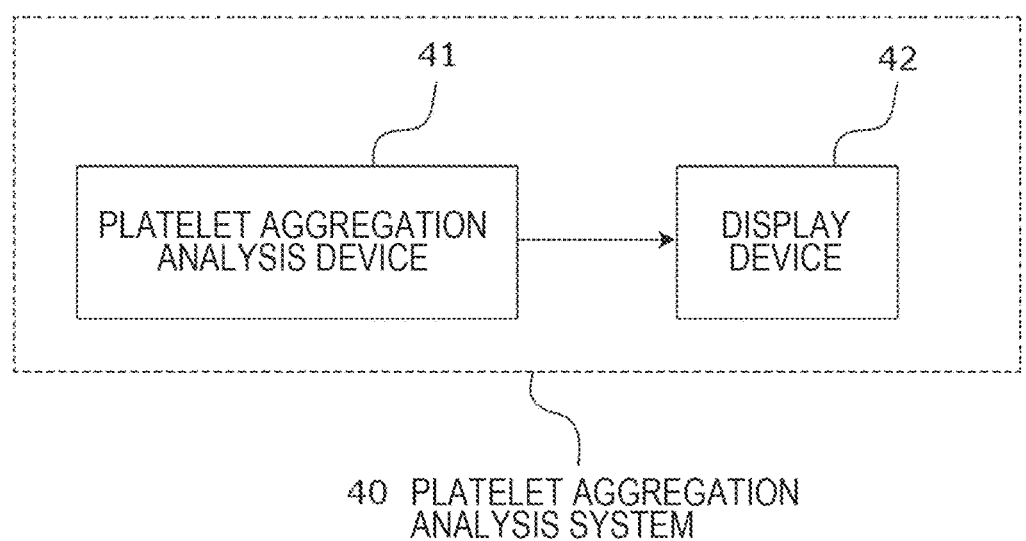
FIG. 4 is a diagram illustrating the outline of a configuration of a platelet aggregation analysis system.

The outline of a platelet aggregation analysis system of the present technology, is illustrated in FIG. 4.

A platelet aggregation analysis system 40 includes the platelet aggregation analysis device 41 described above, and a display device 42 configured to display an analysis result of platelet aggregation.

In the platelet aggregation analysis device 41, a computer with the program for analyzing platelet aggregation, can be incorporated.

A display, a print-out device, or the like, provided in the computer, can be used as the display device 42.

The platelet aggregation analysis device 41 may be configured to analyze not only the platelet aggregation of the platelet-containing specimen but also other blood coagulation system measurement items, or may also function as a blood coagulation system analysis device.

In a case where the platelet aggregation analysis device 41 is used as the blood coagulation system analysis device according to the dielectric constant, and examples of a measurement item include blood coagulation (blood clot), fibrin formation, fibrin clot formation, blood cake formation, rouleau formation, blood aggregation, sedimentation of red blood cells (erythrocyte sedimentation), blood cake retraction (involution), cythemolysis, fibrinolysis, and the like. When such items are analyzed, a program for analyzing such items is used instead of the program for analyzing platelet aggregation, described above.

The display device 42 may include a warning unit. The warning unit sets in advance the range of a normal value in a state change of each blood, and generates a warning when the analysis result of the specimen is out of the range of the normal value. A warning method is not particularly limited, and for example, the warning can be generated by a display or a sound.

EXAMPLES

5. Example

(1) Method

The venous blood of a normal subject was collected according to a normal method by using a commercially available vacuum blood collection tube in which a citric acid was included as an anticoagulation agent. The first one was discarded without being used, and the blood collected subsequent to the first one, was used for the following tests. In addition, the blood was collected, and then, was used after standing to still at a room temperature for approximately 30 minutes.

In dielectric constant measurement, a blood coagulation system analysis device described in the specification of Japanese Patent No. 5691168 and the specification of Japanese Patent No. 5768422 (hereinafter, referred to as a "dielectric coagulometer β machine"), was used. In addition, in impedance aggregation measurement, a platelet function analysis device Multiplate was used.

First, the whole blood of 200 ul was added to a dedicated cartridge for the dielectric coagulometer, into which a platelet-inducing substance and a calcium aqueous solution (0.215M Ca) were put, and was stirred at 37° C. for 5 minutes. In addition, a system to which a normal saline solution was added instead of the platelet-inducing substance, was produced as a control sample, and similarly, the stirring was performed.

Here, adenosine diphosphate (ADP), an arachidonic acid (AA) , and collagen were used as the platelet-inducing substance.

The number of test bodies was N=3.

The blood coagulability measurement according to the dielectricconstant,usingthedielectriccoagulometer β machine, was performed with respect to the blood of the test body. In addition, the impedance aggregation measurement was performed by the platelet function analysis device Multiplate, and thus, an ADP test, an ASPI test, and a COL test were performed. All of the measurements were performed at a temperature of 37° C.

In the method described above, a similar test of a normal subject different from the normal subject described above, was also performed a plurality of times, in order to confirm reproducibility.

(2) Result

Figures 1, 5:
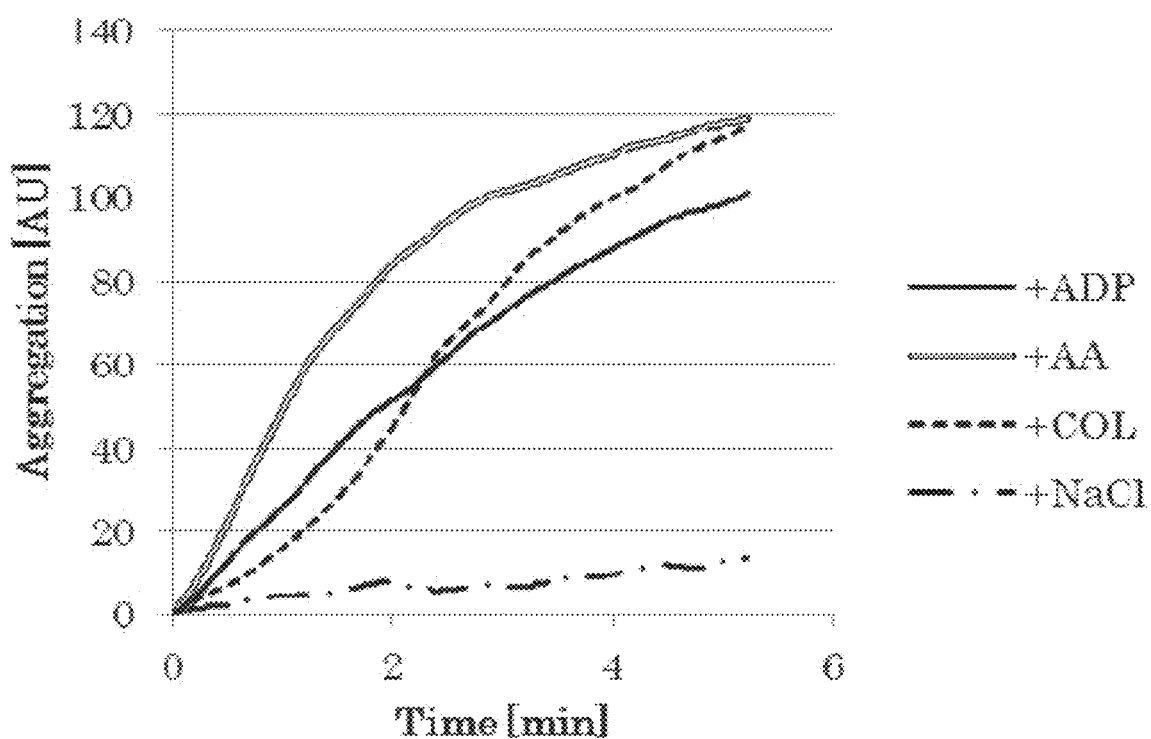
Figures 2, 5:
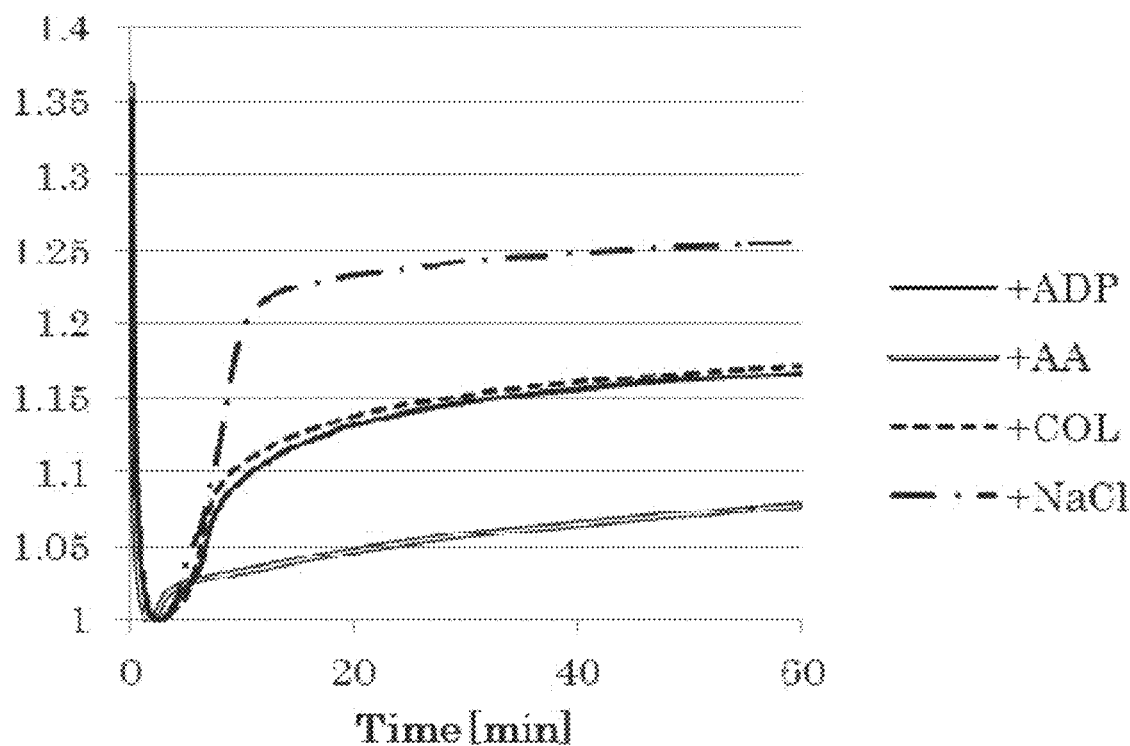

A measurement result of Multiplate that is a platelet aggregation analysis device of the technology of the related art, is shown in FIG. 5-1.

A measurement result of the dielectric coagulometer β machine according to a dielectric constant at 10 MHz, is shown in FIG. 5-2.

In a case where a time change of the assumed result in the dielectric coagulometer β machine, was compared between the addition of the normal saline solution (the control sample) and the addition of the platelet-inducing substance, it was known that a change occurred in an amplitude in a case where the platelet-inducing substance was added.

Such a result correlated with a change in the measurement result of Multiplate, and thus, indicated that it was possible to measure a platelet aggregation reaction even in the dielectric coagulometer β machine.

(3) Analysis Example 1

An example of the analysis method will be described, on the basis of the measurement result according to the dielectric constant in FIG. 5-2 described above.

Figures 1, 6:
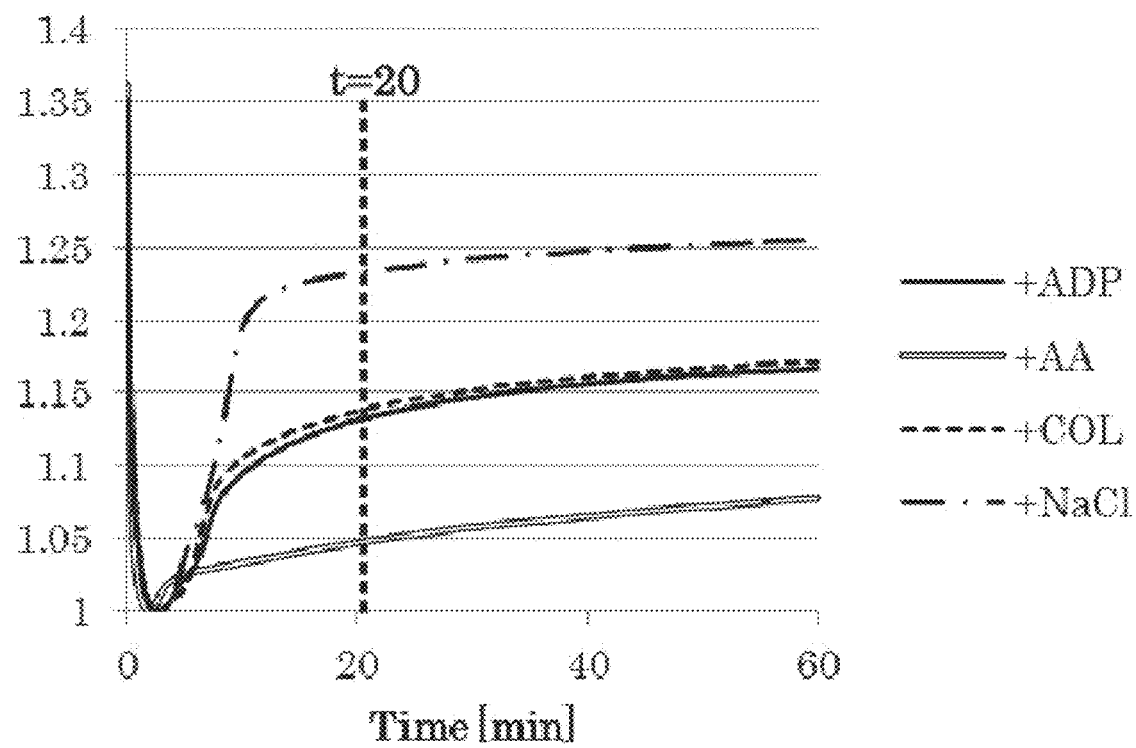
Figures 2, 6:
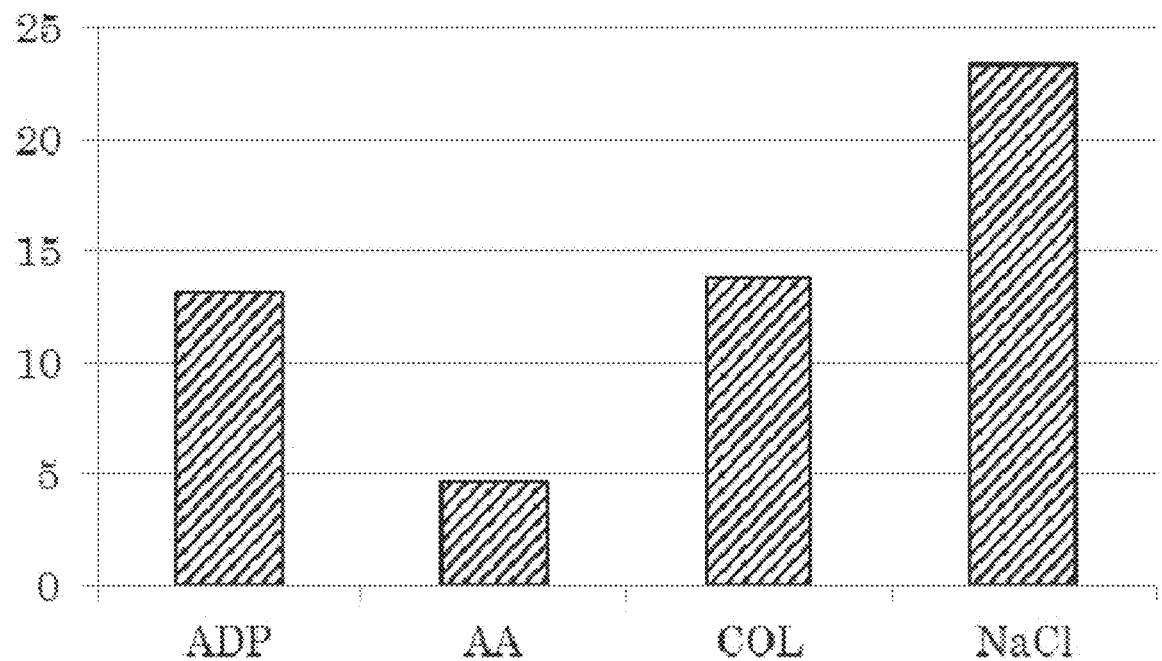

20 minutes when the measurement waveform of the dielectric constant was sufficiently stabilized, was set to a consideration time (FIG. 6-1). A value obtainedby subtracting 1 from a standard value of the time (a minimum value standard), was set to 100 times (correction for not decreasing the value), and the value was defined as CF (FIG. 6-2).

Furthermore, the consideration time is not limited to 20 minutes, and can be shortened to 15 minutes or 10 minutes insofar as a dielectric constant change is stabilized after a coagulation time CT is set. However, it was considered that in a test body in which CT was prolonged, it was necessary to change the definition of the consideration time, according to the CT. Accordingly, there may be a case where the consideration time is after 20 minutes.

In addition, the consideration time can be relatively (dynamically) set with respect to CT without being fixed, and for example, can be CT+X minutes, CT×Y minutes, or a more complex function including CT.

In addition, as shown in FIG. 6-2, a decrease in CF due to the addition of the platelet-inducing substance, was a portion (a platelet contribution portion) reflected by the platelet function, in particular, the aggregation, on the basis of CF of the normal saline solution (NaCl, the control sample), and in a case where the platelet aggregation function decreased or a case where the platelet function inhibitor agent was administered, it was assumed that CT was close to the reference value.

For example, in a patient to whom clopidogrel that is an ADP route inhibitor agent, was administered, a difference from the reference value is small even in a case of adding ADP.

Figures 1, 7:
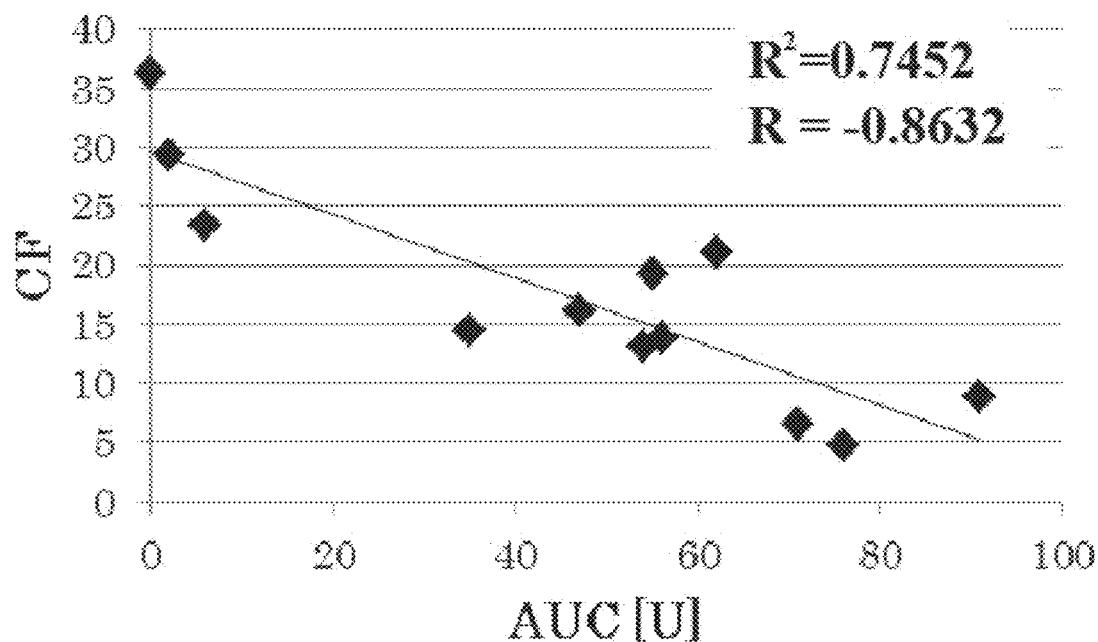
Figures 2, 7:
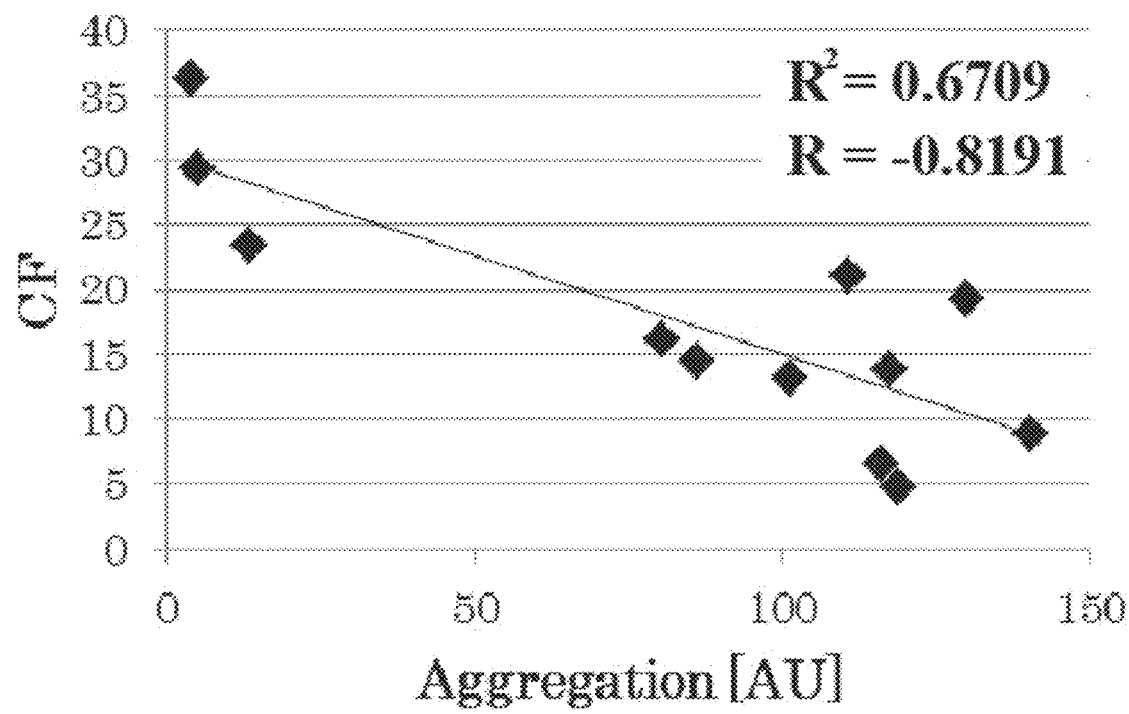

Further, it was confirmed that a CF value had a high correlation with Blood Concentration-Area under Time Curve (AUC(U)) that is a parameter obtained from Multiplate, and aggregation unit (Aggregation (AU)) (FIG. 7-1 and FIG. 7-2). In addition, intergradation of a correlation coefficient in a case where the consideration time is changed (t=5 min, 10 min, 15 min, and 20 min) is shown in Table 1 and Table 2. From Table 1 and Table 2, it is known that in a case where the consideration time is earlier than the determination of CT (t=5 min), the correlation becomes worse, and it is difficult to grasp the platelet contribution portion.

TABLE 1

|  | t = 5 min | t = 10 min | t = 15 min | t = 20 min |
|---|---|---|---|---|
| AUC(U) | −0.32089 | −0.86685 | −0.87283 | −0.86327 |
| Aggregation(AU) | −0.17799 | −0.77917 | −0.83382 | −0.8191 |

TABLE 2

|  | t = 5 min | t = 10 min | t = 15 min | t = 20 min |
|---|---|---|---|---|
| AUC(U) | 0.103 | 0.7514 | 0.7618 | 0.7452 |
| Aggregation(AU) | 0.0317 | 0.6071 | 0.6953 | 0.6709 |

(4) Analysis Example 2

An example of another analysis method will be described, on the basis of the measurement result according to the dielectric constant in FIG. 5-2 described above.

A dielectric clot strength (hereinafter, referred to as "DCS") that is a unique parameter of the blood coagulability measurement according to the dielectric constant, was considered.

DCS is a parameter that can be calculated on the basis of a decrease width from a peak of temporal measurement data measured at a specific frequency.

Specifically, for example, a time when a change in the dielectric constant at a frequency of 10 MHz, is in the vicinity of the minimum value, is defined as a clot time (hereinafter, referred to as "CT") , DCS is calculated from a dielectric constant difference when the coagulation is ended with respect to a dielectric constant at a CT time (an end point). The setting of the end point is changed, and thus, various DCS parameters can be calculated. Here, the end point was set to a point of the maximum gradient of 10% of an inclination of a dielectric constant change after CT was determined at 10 MHz.

Figure 8:
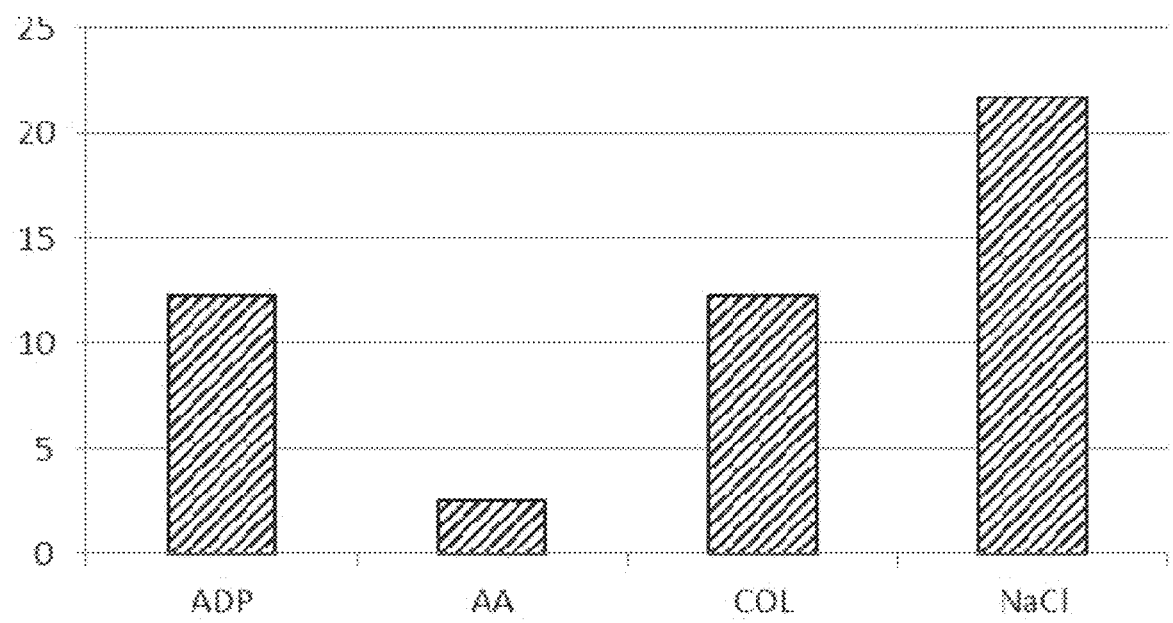
FIG. 8 is a graph showing a dielectric clot strength of a platelet-inducing substance-added test body and a control sample.

In FIG. 8, a graph of DCS of a test body to which calcium chloride and the platelet-inducing substance were added, and DCS of a control sample to which calcium chloride and sodium chloride (a normal saline solution) were added, is shown.

In the graph of FIG. 8, a change similar to that of the graph of FIG. 6-2, was observed, and thus, it was known that information (the platelet contribution portion) reflected by the platelet function, in particular, the aggregation was capable of being obtained by calculating DCS.

Figures 1, 9:
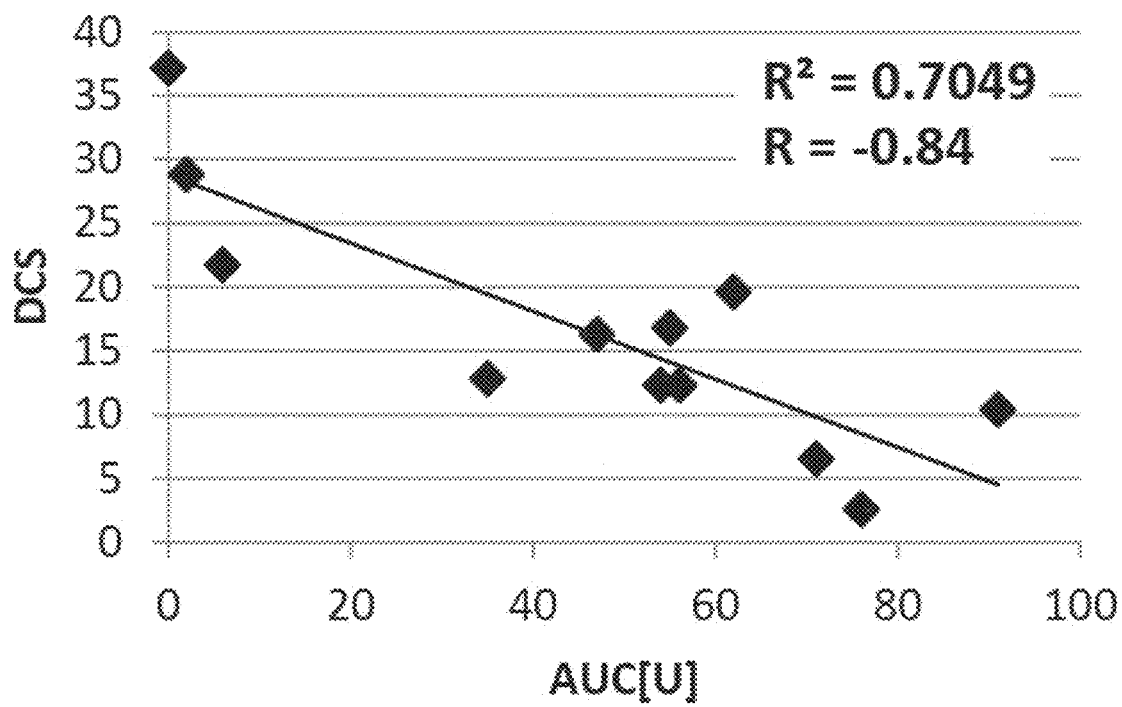
Figures 2, 9:
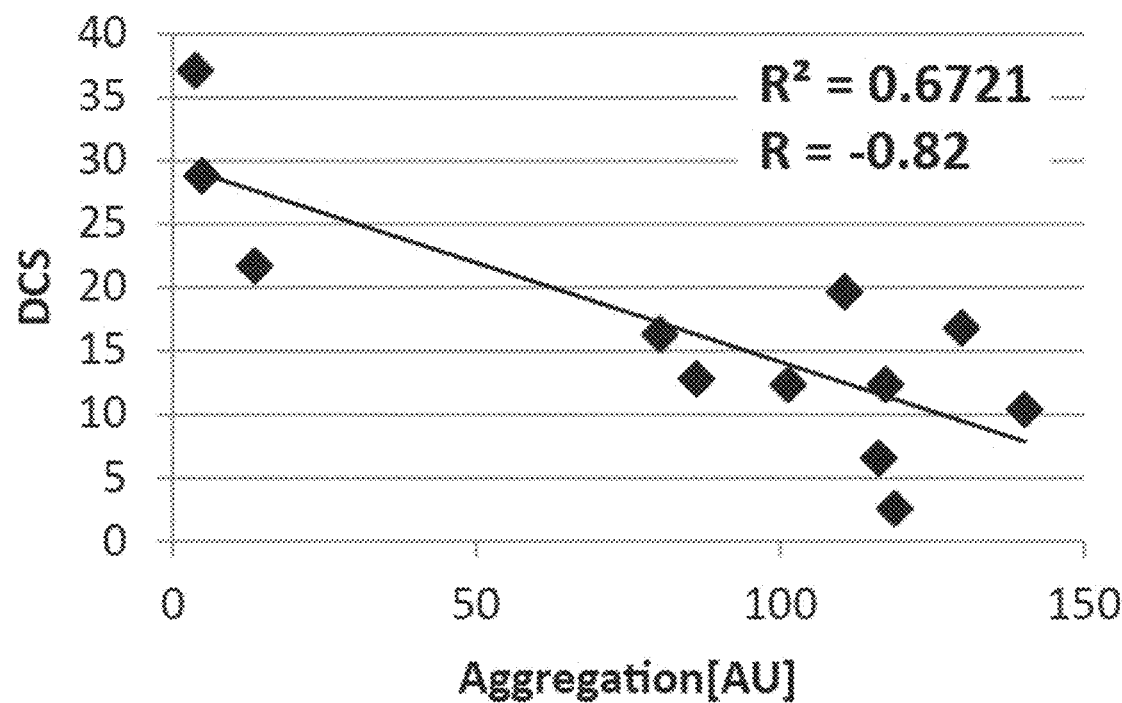

In addition, it was confirmedthat DCS hada high correlation with AUC(U) that is a parameter obtained from Multiplate, and Aggregation (AU) (FIG. 9-1 and FIG. 9-2).

As described above, DCS is a parameter that can be calculated on the basis of a decrease width from a peak of temporal measurement data measured at a specific frequency (for example, 1 MHz) , and may be calculated by using a width of a change in a dielectric constant at 10 MHz, or the like.

6. Conclusion

The present technology is, as a clinical examination having thrombosis in view, capable of measuring and analyzing the platelet aggregation in the whole blood that is a more excellent specimen.

In addition, in the related art, when the platelet aggregation and the blood coagulability are measured, different measurement technologies are used for each measurement, and thus, separate measurement devices are required, but according to the present technology, it is possible to perform the platelet aggregation measurement and the measurement relevant to a coagulation factor, by the same device.

For example, in a case where a plurality of measurement units configured to perform simultaneous measurement, is provided in the device of the present technology, the control sample to which the sodium salt is added, and the specimen to which the sodium salt and the platelet-inducing substance are added, are measured, and the platelet aggregation is examined, and simultaneously, a specimen to which an extrinsic and intrinsic coagulation accelerating agent is added, is measured, and thus, it is possible to examine the blood coagulability. According to such a device, it is possible to investigate a mutual relationship between the platelet aggregation and the blood coagulability.

Further, the present technology is useful in monitoring of a patient who is dosed with an antiplatelet aggregation agent and/or an anticoagulation agent, monitoring of a blood state of a patient during an operation, or the like.

For example, in a case where only the platelet is activated by the platelet-inducing substance, DCS described above is a value lower than that of the control sample (the normal saline solution). This is a change according to platelet contribution, and indicates that the platelet function increases as DCS decreases due to the addition of the platelet-inducing substance. In addition, in a case where DCS is high (a high value) identical to or close to that of the control sample regardless of the addition of the platelet-inducing substance, it is possible to presume that the platelet function decreases or there is a possibility that an antiplatelet agent is administered.

Furthermore, the present technology is capable of having the following configurations:

[1] A platelet aggregation analysis method, including:
a step of adding a platelet-inducing substance and a calcium salt to a platelet-containing specimen;
a step of stirring the platelet-containing specimen; and
a step of acquiring measurement data of an electrical characteristic and/or viscoelasticity of the platelet-containing specimen.

[2] The platelet aggregation analysis method described in [1],
in which the measurement data of the electrical characteristic is a dielectric constant of the platelet-containing specimen.

[3] The platelet aggregation analysis method described in [1],
in which the measurement data of the viscoelasticity is measurement data of the platelet-containing specimen according to a rheometer.

[4] The platelet aggregation analysis method described in [1] or [2], further including:
a step of analyzing platelet aggregation, on the basis of the measurement data of the electrical characteristic and/or the viscoelasticity of the platelet-containing specimen, and measurement data of an electrical characteristic and/or viscoelasticity, acquired from a platelet-containing specimen to which the platelet-inducing substance is not added.

[5] The platelet aggregation analysis method described in any one of [1] to [4],
in which the platelet-containing specimen is blood or blood plasma.

[6] The platelet aggregation analysis method described in [5],
in which the blood or the blood plasma is collected from a test subject dosed with an antiplatelet aggregation agent and/or an anticoagulation agent.

[7] A platelet aggregation analysis device, including:
a biological sample retention unit configured to retain a platelet-containing specimen;
a medical agent supply unit configured to supply a platelet-inducing substance and/or a calcium salt to the platelet-containing specimen;
a stirring mechanism configured to stir the platelet-containing specimen; and
a measurement unit configured to measure an electrical characteristic of the platelet-containing specimen.

[8] A program for analyzing platelet aggregation, allowing a computer to execute:
analyzing platelet aggregation, on the basis of measurement data of an electrical characteristic and/or viscoelasticity, acquired from a platelet-containing specimen to which a platelet-inducing substance and a calcium salt are added, and measurement data of an electrical characteristic and/or viscoelasticity, acquired from a platelet-containing specimen to which the platelet-inducing substance is not added.

[9] The program for analyzing platelet aggregation described in [8],
in which the analyzing includes comparing the measurement data of the electrical characteristic and/or the viscoelasticity, acquired from the platelet-containing specimen to which the platelet-inducing substance and the calcium salt are added, with the measurement data of the electrical characteristic and/or the viscoelasticity, acquired from the platelet-containing specimen to which the platelet-inducing substance is not added.

[10] A platelet aggregation analysis system, including:
a platelet aggregation analysis device including:
a biological sample retention unit configured to retain a platelet-containing specimen;

a medical agent supply unit configured to supply a platelet-inducing substance and/or a calcium salt to the platelet-containing specimen; a stirring mechanism configured to stir the platelet-containing specimen; and a measurement unit configured to measure an electrical characteristic of the platelet-containing specimen, a computer with a program for analyzing platelet aggregation being built in the platelet aggregation analysis device, the program allowing the computer to execute analyzing platelet aggregation, on the basis of measurement data of the electrical characteristic and/or viscoelasticity, acquired from the platelet-containing specimen to which the platelet-inducing substance and the calcium salt are added, and measurement data of an electrical characteristic and/or viscoelasticity, acquired from a platelet-containing specimen to which the platelet-inducing substance is not added; and a display device configured to display an analysis result.

REFERENCE SIGNS LIST

1 Biological sample retention unit
2 Biological sample supply unit
3 Medical agent supply unit
4 Temperature control unit
5 Time control unit
6 Stirring mechanism
7 Driving mechanism
8 Measurement unit
9 Measurement condition control unit
10 Accuracy management unit
11 Analysis unit
40 Platelet aggregation analysis system
41 Platelet aggregation analysis device
42 Display device

The invention claimed is:

1. A platelet aggregation analysis method, comprising:
adding a platelet-inducing substance and a calcium salt to a first platelet-containing specimen;
acquiring first measurement data of an electrical characteristic and/or viscoelasticity of the first platelet-containing specimen;
acquiring second measurement data of the electrical characteristic and/or viscoelasticity of a second platelet-containing specimen to which the platelet-inducing substance is not added; and
analyzing platelet aggregation, on a basis of the first measurement data of the electrical characteristic and/or the viscoelasticity of the first platelet-containing specimen, and the second measurement data of the electrical characteristic and/or viscoelasticity of the second platelet-containing specimen, wherein analyzing platelet aggregation includes extracting a characteristic point from the first and second measurement data and determining a difference between the first measurement data and the second measurement data at the extracted characteristic point and wherein a magnitude of the difference between the first measurement data and the second measurement data at the extracted characteristic point is indicative of an amount of platelet aggregation.

2. The platelet aggregation analysis method according to claim 1,
wherein the measurement data of the electrical characteristic is a dielectric constant of the platelet-containing specimen.

3. The platelet aggregation analysis method according to claim 1,
wherein the measurement data of the viscoelasticity is measurement data of the platelet-containing specimen according to a rheometer.

4. The platelet aggregation analysis method according to claim 1,
wherein the platelet-containing specimen is blood or blood plasma.

5. The platelet aggregation analysis method according to claim 4,
wherein the blood or the blood plasma is collected from a test subject dosed with an antiplatelet aggregation agent and/or an anticoagulation agent.

6. The platelet aggregation analysis method according to claim 1, further comprising stirring the platelet-containing specimen.

7. A platelet aggregation analysis device, comprising:
a biological sample retention unit configured to retain a platelet-containing specimen;
a medical agent supply unit configured to supply a platelet-inducing substance and/or a calcium salt to the platelet-containing specimen;
a measurement unit configured to measure an electrical characteristic of the platelet-containing specimen; and
an analysis unit configured to analyze platelet aggregation, on a basis of first measurement data of the electrical characteristic and/or the viscoelasticity, acquired from a first platelet-containing specimen to which the platelet-inducing substance and the calcium salt are added and second measurement data of the electrical characteristic and/or viscoelasticity, acquired from a second platelet-containing specimen to which the platelet-inducing substance is not added, wherein analyzing platelet aggregation includes extracting a characteristic point from the first and second measurement data and determining a difference between the first measurement data and the second measurement data at the extracted characteristic point and wherein a magnitude of the difference between the first measurement data and the second measurement data at the extracted characteristic point is indicative of an amount of platelet aggregation.

8. The platelet aggregation analysis device according to claim 7, further comprising a stirring mechanism configured to stir the platelet-containing specimen.

9. A non-transitory computer readable medium storing instructions that, when executed by a computer, perform a method for analyzing platelet aggregation comprising:
analyzing platelet aggregation, on a basis of first measurement data of an electrical characteristic and/or viscoelasticity, acquired from a first platelet-containing specimen to which a platelet-inducing substance and a calcium salt are added, and second measurement data of the electrical characteristic and/or viscoelasticity, acquired from a second platelet-containing specimen to which the platelet-inducing substance is not added, wherein analyzing platelet aggregation includes extracting a characteristic point from the first and second measurement data and determining a difference between the first measurement data and the second measurement data at the extracted characteristic point and wherein a magnitude of the difference between the first measurement data and the second measurement data at the extracted characteristic point is indicative of an amount of platelet aggregation.

10. A platelet aggregation analysis system, comprising:
a platelet aggregation analysis device including:
- a biological sample retention unit configured to retain a platelet-containing specimen;
- a medical agent supply unit configured to supply a platelet-inducing substance and/or a calcium salt to the platelet-containing specimen;
- a measurement unit configured to measure an electrical characteristic of the platelet- containing specimen; and an analysis unit configured to analyze platelet aggregation, on a basis of first measurement data of the electrical characteristic and/or viscoelasticity, acquired from a first platelet-containing specimen to which the platelet-inducing substance and the calcium salt are added, and second measurement data of the electrical characteristic and/or viscoelasticity, acquired from a second platelet-containing specimen to which the platelet-inducing substance is not added, wherein analyzing platelet aggregation includes extracting a characteristic point from the first and second measurement data and determining a difference between the first measurement data and the second measurement data at the extracted characteristic point and wherein a magnitude of the difference between the first measurement data and the second measurement data at the extracted characteristic point is indicative of an amount of platelet aggregation; and a display device configured to display an analysis result.

11. The platelet aggregation analysis system according to claim 10, wherein the platelet aggregation analysis device further comprises a stirring mechanism configured to stir the platelet-containing specimen.

* * * * *